United States Patent [19]
Glattstein

[11] Patent Number: 6,133,040
[45] Date of Patent: Oct. 17, 2000

[54] PROCESS AND TEST KIT FOR COCAINE DETECTION

[75] Inventor: Baruch Glattstein, Jerusalem, Israel

[73] Assignee: Identa, Ltd., Jerusalem, Israel

[21] Appl. No.: 08/860,435

[22] PCT Filed: Dec. 27, 1995

[86] PCT No.: PCT/EP95/05143

§ 371 Date: Aug. 28, 1997

§ 102(e) Date: Aug. 28, 1997

[87] PCT Pub. No.: WO96/20405

PCT Pub. Date: Jul. 4, 1996

[30] Foreign Application Priority Data

Dec. 26, 1994 [IL] Israel ......................................... 112152

[51] Int. Cl.⁷ .................................................... G01N 33/00
[52] U.S. Cl. .............................. 436/92; 436/96; 436/901; 436/164; 422/61
[58] Field of Search .............................. 436/92, 96, 901, 436/164; 422/61

[56] References Cited

U.S. PATENT DOCUMENTS 4,840,912  6/1989  Glattstein .................................. 436/92
5,498,547  3/1996  Blake et al. ............................. 436/111

FOREIGN PATENT DOCUMENTS 233063  8/1987  European Pat. Off. .

OTHER PUBLICATIONS

T. Sakai et al., Chem Pharm. Bull., vol. 24, No. 11, 1976, pp. 2883–2886.

L.J. Scott, Jr., DEA Lab. Notes, No. 68, 1973, pp. 179–181.

*Primary Examiner*—Lyle A. Alexander
*Attorney, Agent, or Firm*—Birch, Stewart, Kolasch & Birch, LLP

[57] ABSTRACT

Test kit and method for discriminating cocaine and its salts from substances that falsely give a positive color reaction with Scott's thiocyanate reagent. As all Scott false positive substances have lower pKa values than cocaine, or in their basic from higher pKa values than the cocaine base, they can be discriminated from cocaine by a suitable pH test of the solution. The pH indicator is preferably organic or lipophilic so that it can be dissolved in a solvent immiscible with water. The partitioning of the organic cocaine base or its salt between an organic and water phase of specific pH is used to further distinguish the test substance.

9 Claims, No Drawings

PROCESS AND TEST KIT FOR COCAINE DETECTION

FIELD OF THE INVENTION

The present invention relates to a process and test kit for detection and identification of cocaine, more specifically, cocaine and "crack", which do not give false positive results with other substances.

BACKGROUND OF THE INVENTION

As illicitly manufactured drugs are marketed and transferred from hand to hand without any manufacturer's identification and specification and as it is not possible to distinguish visually sugar, salt, heroin, crack, and cocaine, it is necessary to examine the presumptive drug substances in a laboratory. The crime laboratories, however, are often very busy so that such drug tests may take too long to keep the suspects meanwhile in custody. Many police agencies have therefore turned to test the presumptive drugs themselves. Thus, chemical spot test kits have been commercially developed which shall allow an easy identification of narcotics and drugs of abuse. Many law enforcement agencies are using these kits as the investigator can now easily check the suspected drug substances within minutes. Conventional test kits for detection and identification of cocaine are commonly based on contacting the suspected substance with a cobalt thiocyanate solution. The formation of a relatively water insoluble turquoise complex indicates the presence of cocaine or its salts. As the cobalt thiocyanate test is relatively simple, it is also in use outside the laboratories. Notwithstanding, there is a great demand for a more specific test kit.

The standard Scott test is based on a colour reaction with cobalt thiocyanate (L. J. SCOTT (1973), *Specific Field Test For Cocaine*, Microgram, VI, 179). The corresponding commerical test kit contains the necessary chemicals in three prefilled hermetically sealed glass ampules or tubes and comprises the following steps:

Step A. The first tube contains cobalt thiocyanate in a solution of 1:1 water and glycerine which forms a characteristic blue precipitate with salts of cocaine.

When the cobalt thiocyanate is dissolved in water alone, a blue precipitate is formed with nearly every alkaloid substance. The addition of glycerine (1:1) to the aqueous reagent, however, reduces the solubility of most drug substances other than cocaine to almost zero, so that these other substances cannot participate in a falsely positive colour reaction. By this way, it is possible to exclude drugs such as heroin, methadone, quinine etc. However, cocaine stays soluble in such a mixture of water and glycerine and can give a good response.

Crack, which is a cocaine base, reacts with Scott's reagent slower and with less colour intensity. The addition of acid, however, converts crack to its salt and enhances its colour reaction.

L. J. Scott reports that four drugs in this stage will react with the same colour reaction as cocaine: (1) phencyclidine (PCP); (2) dibucaine; (3) butacaine; (4) methapyrilene. The two steps below shall exclude these four drugs:

Step B. By adding concentrated hydrochloric acid, the initially blue solution is converted into a clear pink solution.

Step C. By adding chloroform the blue complexed cocaine is partitioned into the organic phase.

The Scott test has several disadvantages. L. J. Scott himself reports that (i) the ratio of solution A to B is critical. When an excessive amount of hydrochloric acid (solution B) is added to solution A, after the colour reaction with cocaine, a blue rather than a pink solution is formed, and the blue will no longer be extractable into the chloroform layer after the addition of solution C. (ii) On the other hand, when an excessive amount of cocaine is present in step A, it can be sometimes necessary to add two additional drops of hydrochloric acid which makes the test prone to errors. (iii) Furthermore, Scott has only tested a limited number of drugs. Since then, it has been found that also some other compounds can give a blue colour with Scott's reagent, e.g. dixyrazine.

With the cobalt thiocyanate reagent of ODV Inc., which is hereafter called "Scott's modified reagent", procaine, tetracaine and methadone give a colour reaction similar to cocaine. Thus, this single reagent cannot really serve as a specific colour reagent for the identification of cocaine, since false positive results are also obtained with substances that have similar response characteristics.

The European Patent No. 0 233 063 discloses a process and kit for the presumptive identification of cocaine or heroine street drugs. This process comprises applying to the sample to be tested a reagent, comprising a sulfonated aromatic pH indicator which gives a characteristic colour reaction in the presence of trace amounts of organic bases or acetic acid. The process provides a quick test for the detection of street drugs which can then, for example, be followed by the Scott's test. In order to deal with the increasing number of similar street drugs, i.e. in their base form, it has become necessary to combine several tests to exclude false positive results.

The deficiencies of these tests have led the inventor to develop another specific reagent, which is intended to be used in combination with Scott's reagent or Scott's modified reagent, in order to screen out false positive results in the Scott reaction. This other specific reagent allows surprisingly an error-free positive identification of cocaine and its salts.

SUMMARY OF THE INVENTION

In accordance with the invention there is provided a process for the differentiation of cocaine and/or its salts from other substances that may react with Scott's cobalt thiocyanate reagent or Scott's modified reagent similar as cocaine and its salts. This is accomplished by applying to a sample of the suspected drug a reagent which gives a characteristic colour reaction in the presence of trace amounts of cocaine and its salts and another colour reaction with false positive substances.

The present invention also provides a kit for cocaine detection comprising:

a) Scott's cobalt thiocyanate reagent or Scott's modified reagent;

b) a pH indicator solution which has a distinctive colour in the presence of cocaine and another, different colour in case of a substance giving a false positive result with Scott's reagent or Scott's modified reagent wherein the indicator is dissolved in a solvent immiscible with water; and c) a buffer solution of pH 7 for partitioning the organic base to the organic phase.

DETAILED DESCRIPTION OF THE INVENTION

Contrary to the prior art approach for the detection of cocaine and its salts, it has been found that cocaine and its salts, i.e. cocaine and crack, in a powder can be differentiated by its basic character from substances that give with cobalt thiocyanate a false positive colour reaction.

Cocaine belongs to a class of natural products known as alkaloids; this term is used to designate nitrogen-containing compounds of vegetable origin which commonly have a heterocyclic ring system and one or more basic nitrogen atoms. The basicity is a fundamental property of these substances which all have at least one nitrogen atom; it is affected by the aromatic and aliphatic character and by the substituents. Electron releasing substituents like $CH_3$ increase and electron withdrawing substituents like COOH or COOR decrease the basicity.

Cocaine is a very weak base. It comprises a tropane structure and a nitrogen carrying three alkyl substituents. Nevertheless, the basic character of this nitrogen is very weak, probably, because of a combination of steric factors and its two esters which are electron withdrawing substituents. The pKa of cocaine is 5.6.

All substance that give false positive results with Scott's reagent or the Scott's modified reagent have a much stronger basic character, except for lidocain which is less basic than cocaine. In particular:

(A) PCP comprises a piperidine ring which has strong basic character. Piperidine has a pKa of 11.1, and 1-ethyl piperidine, which is a better analog to PCP, has a pKa of 10.45.
(B) Dibucaine is a strong base because of its triethylamine group. Triethylamine has a pKa of 11.01.
(C) Butacaine is also a strong base. It has a dibutylpropylamine group which has a pKa similar to dibucaine.
(D) Methapyrilene is a strong base because it has a trimethylamine group. Trimethylamine has a pKa of 9.81.
(E) Dixyrazine is a strong base because of its piperazine group. Piperazine has a pKa of 9.83.
(F) Lidocaine is a very weak base because of its acetamido group.

The following substances also produce false positive reactions with Scott's modified reagent:
(A) Procaine has a triethylamine group as dibucaine.
(B) Methadone is a strong base and it has dimethylpropylamine group with a pKa greater than 10.
(C) Tetracaine is a strong base as well. It has dimethylamine group whose pKa is 10.73.

The method according to the invention is preferably carried out with an organic and/or lipophilic pH indicator reagent which produces a distinctive colour reaction in the presence of trace amounts of cocaine. The indicator does not react or give another colour reaction with substances that have a different (higher or lower) basicity than cocaine, and which react with Scott's reagent or Scott's modified reagent.

Preferably, the lipophilic pH indicator is selected from phthalein indicators such as tetrabromophenolphthalein ethyl ester and naphtholphthalein.

The colour reaction of the lipophilic pH indicator is preferably done in two steps:

First, a small amount of the indicator is dissolved in a solvent immiscible with water, for example in chloroform, dichloromethane or 1,2-dichloroethane. A trace amount of the suspected cocaine is then placed in a test tube, and a few drops of the indicator solution added. The solution is observed because a free organic base will cause a change in colour in dependence of the characteristics of the indicator and the basicity of the base.

Second, when there is no change in colour, a few drops of an aqueous buffer of pH 7 are added and the solution is observed once again. If a salt of an organic base is present, the organic base will be partitioned to the organic phase and react with the indicator, which can be observed.

EXAMPLE 1

About 25 mg of tetrabromophenolphthalein ethyl ester (TBP) is dissolved in 100 ml dichloromethane, giving a yellow solution. A trace amount of the suspected cocaine is added to a small test tube, after a part of the substance has been tested positive with Scott's reagent or Scott's modified reagent. Even a substance that has been reacted with Scott's reagent may be used. A few drops of TBP reagent are added to the test tube. An immediate intensive green colour confirms the presence of "crack" (cocaine base).

If there was no change in colour, a few drops of the aqueous buffer pH 7 are added. If the suspected substance is a cocaine salt, a green colour instantly appears in the lower phase (dichloromethan phase).

Reacting the indicator solution with a larger amount (a few milligrams) of cocaine gave a more intensive green colour reaction.

Substances reacting falsely positive with Scott's reagent gave in this method the following colour reactions:

Trace amounts (<1 mg) of PCP, dibucaine, methapyrilene, butacaine, dixyrazine, tetracaine, procaine and methadone gave a red colour. With a larger amount, a purple colour was observed. Lidocain gave no change of colour or, if at all, a very faint yellow-brown colour.

The above-identified indicators behave in this example as follows:

First, when using a high concentration of the indicator (50 mg/100 ml dichloromethan) a red colour reaction like for Scott false positive substances is observed, even when a few milligrams of cocaine are present. However, trace amounts of cocaine (<1 mg) give a green colour. All false positive substances give a red or purple colour reaction.

On the other hand, when using a low concentration of the indicator (5 mg/100 ml dicloromethan) and a few milligrams of cocaine in the reaction mixture, the colour reaction is blue, whereas all the false positive substances give a red or purple colour reaction, except for lidocaine which gives no or a very faint, easily distinguishable yellow-brown colour.

When trace amounts of cocaine (<1 mg) are present, a green colour is observed whereas under the same conditions the false positive substances give a red or purple colour reaction. It is essential therefore, to use a proper concentration of the indicator and to have a sample with only trace amounts of the cocaine.

Second, when a basic buffer is used, the same results can be observed in the chloroform layer but the buffer solution is blue.

Third, when an acidic buffer is used, no colour reaction is observed with cocaine.

EXAMPLE 2

Naphtholphthalein was used as the indicator. 25 mg of the indicator was dissolved in 50 ml of chloroform. The solution had no colour. The procedure was similar as above. Results: With "crack" and cocaine the chloroform solution remained colourless. All the other drugs mentioned above gave a yellow chloroform solution. The results can be commented as follows: First, the indicator is less sensitive than TBP and, second, by using a basic buffer the indicator is extracted into the buffer layer.

What is claimed is:

1. A process for discriminating cocaine and/or its salts from substances that give a false positive result in a Scott test comprising the following steps:
   a) reacting a substance with a cobalt thiocyanate reagent or Scott's thiocyanate reagent;
   b) applying to a substance that gives a positive result in step a) a solution containing a phthalein pH indicator, wherein
      (1) when said substance is a cocaine base the solution turns a cocaine-indicative color or does not change color, or
      (2) when said substance is a substance giving a false positive result with Scott's test reagents the solution turns a color which is distinguishable from said cocaine-indicative color; and
   c) adding a few drops of an aqueous buffer solution of pH 7, if there has been no change in the color of the indicator solution of step b), wherein
      (1) when cocaine salts are present the resulting solution appears said cocaine-indicative color, or
      (2) when substances giving false positive results with Scott's test reagents are present, the resulting solution is a color distinguishable from said cocaine indicative-color.

2. The process according to claim 1, wherein the phthalein indicator is lipophilic or organic or both.

3. The process according to claim 1, wherein the phthalein indicator is tetrabromophenolphthalein ethylester or naphtholphthalein.

4. The process according to claim 1, wherein the color reaction of the phthalein indicator is done in two steps:
   a) dissolving a small amount of the phthalein indicator in a solvent immiscible with water and adding a few drops of said indicator solution to the test substance so there is a change in color of the solution when an organic free base is present; and
   b) adding a few drops of aqueous buffer of pH 7 if there is no change in the color of the solution in step a), and when there is a salt of an organic base, the organic base is partitioned into the organic phase to produce a solution that is either said cocaine-indicative color or a color distinguishable from said cocaine-indicative color.

5. The process according to claim 4, wherein the solvent immiscible in water is chloroform, dichloromethane or 1,2-dichloroethane.

6. The process according to claim 1 for testing trace amounts of cocaine and/or its salts in the range of less than 1 mg.

7. The process according to claim 1 for discriminating cocaine and/or its salts from phencyclidine, dibucaine, butacaine, methapyrilene, dixyrazine and lidocaine.

8. The process according to claim 1 for discriminating cocaine and/or its salts from procaine, tetracaine and methadone.

9. A kit for detection and identification of cocaine and/or its salts and for use in a process according to claim 1, comprising:
   a) a cobalt thiocyanate reagent or Scott's thiocyanate reagent;
   b) a pH indicator solution wherein the indicator is dissolved in a solvent immiscible with water and wherein said solution turns said cocaine-indicative color or does not change color in the presence of cocaine or turns a color distinguishable from said cocaine-indicative color in the presence of substances giving a false positive result in Scott's test; and
   c) an aqueous buffer of pH 7 for transferring an organic base to the organic phase.

* * * * *